(12) United States Patent
Lee et al.

(10) Patent No.: US 8,008,454 B2
(45) Date of Patent: Aug. 30, 2011

(54) FUSION PROTEIN HAVING THE ENHANCED IN VIVO ACTIVITY OF ERYTHROPOIETIN

(75) Inventors: Dong-Eok Lee, Seoul (KR); Myung-Suk Oh, Ichon-Shi (KR); Ki-Wan Kim, Seoul (KR); Bo-Sup Chung, Anyang-Shi (KR); Byung-Jhip Ha, Yongin-Shi (KR); Ji-Sook Park, Seoul (KR)

(73) Assignee: CJ CheilJedang Corporation, Seoul (KR)

( * ) Notice: Subject to any disclaimer, the term of this patent is extended or adjusted under 35 U.S.C. 154(b) by 2556 days.

(21) Appl. No.: 10/433,508

(22) PCT Filed: Dec. 10, 2001

(86) PCT No.: PCT/KR01/02137
§ 371 (c)(1),
(2), (4) Date: Jun. 3, 2003

(87) PCT Pub. No.: WO02/48194
PCT Pub. Date: Jun. 20, 2002

(65) Prior Publication Data
US 2009/0221037 A1    Sep. 3, 2009

(30) Foreign Application Priority Data

Dec. 11, 2000 (KR) .................. 2000-75230
Nov. 21, 2001 (KR) .................. 2001-72713

(51) Int. Cl.
*C07K 1/00* (2006.01)
*C07H 21/04* (2006.01)

(52) U.S. Cl. ................... 530/397; 536/23.51
(58) Field of Classification Search .............. None
See application file for complete search history.

(56) References Cited

U.S. PATENT DOCUMENTS

| 5,585,345 | A | | 12/1996 | Boime |
| 5,712,122 | A | * | 1/1998 | Boime et al. ............... 435/69.7 |
| 5,759,818 | A | | 6/1998 | Boime |
| 5,792,460 | A | | 8/1998 | Boime |

FOREIGN PATENT DOCUMENTS

EP          640619  A1    3/1995

OTHER PUBLICATIONS

Matzuk et al., Site specificity of the Chorionic gonadotropin N-Linked oligosaccharides in Signal Transduction., The Journal of Biological Chemistry, 1989, vol. 264, pp. 2409-2414.*
PDB 1QFW_B (last viewed on Jul. 23, 2010).*
Matzuk et al., The Role of theasparagine-linked Oligosaccharides of the α Subunit in the Secretion and Assembly of Human Chorionic Gonadotropin., The Journal of Cell Biology, 1988, vol. 106, pp. 1049-1059.*

* cited by examiner

*Primary Examiner* — Alexander Kim
(74) *Attorney, Agent, or Firm* — Peter F. Corless; Christine C. O'Day; Edwards Angell Palmer & Dodge LLP (57) ABSTRACT

The present invention relates to a fusion protein in which a carboxy terminal of human erythropoietin (EPO) is fused with a carboxy terminal peptide fragment of β subunit of human chorionic gonadotropin (HCG), to DNA encoding the fusion protein, and to a method for preparation of the fusion protein. The fusion protein has the enhanced in vivo activity of erythropoietin.

4 Claims, 7 Drawing Sheets

Fig. 1

```
1                                                          10
TCC TCT TCC TCA AAG GCC CCT CCC CCC AGC CTT CCA AGC CCA TCC
Ser Ser Ser Ser Lys Ala Pro Pro Pro Ser Leu Pro Ser Pro Ser 20                           28
CGA CTC CCG GGG CCC TCG GAC ACC CCG ATC CTC CCA CAA
Arg Leu Pro Gly pro Ser Asp Thr Pro Ile Leu Pro Gln
```

Fig. 2

```
ATG GGG GTG CAC GAA TGT CCT GCC TGG CTG TGG CTT CTC CTG TCC
MET Gly Val His Glu Cys Pro Ala Trp Leu Trp Leu Leu Leu Ser

CTG CTG TCG CTC CCT CTG GGC CTC CCA GTC CTG GGC GCC CCA CCA
Leu Leu Ser Leu Pro Leu Gly Leu Pro Val Leu Gly Ala Pro Pro

CGC CTC ATC TGT GAC AGC CGA GTC CTG GAG AGG TAC CTC TTG GAG
Arg Leu Ile Cys Asp Ser Arg Val Leu Glu Arg Tyr Leu Leu Glu

GCC AAG GAG GCC GAG AAT ATC ACG ACG GGC TGT GCT GAA CAC TGC
Ala Lys Glu Ala Glu Asn Ile Thr Thr Gly Cys Ala Glu His Cys

AGC TTG AAT GAG AAT ATC ACT GTC CCA GAC ACC AAA GTT AAT TTC
Ser Leu Asn Glu Asn Ile Thr Val Pro Asp Thr Lys Val Asn Phe

TAT GCC TGG AAG AGG ATG GAG GTC GGG CAG CAG GCC GTA GAA GTC
Tyr Ala Trp Lys Arg MET Glu Val Gly Gln Gln Ala Val Glu Val

TGG CAG GGC CTG GCC CTG CTG TCG GAA GCT GTC CTG CGG GGC CAG
Trp Gln Gly Leu Ala Leu Leu Ser Glu Ala Val Leu Arg Gly Gln

GCC CTG TTG GTC AAC TCT TCC CAG CCG TGG GAG CCC CTG CAG CTG
Ala Leu Leu Val Asn Ser Ser Gln Pro Trp Glu Pro Leu Gln Leu

CAT GTG GAT AAA GCC GTC AGT GGC CTT CGC AGC CTC ACC ACT CTG
His Val Asp Lys Ala Val Ser Gly Leu Arg Ser Leu Thr Thr Leu

CTT CGG GCT CTG GGA GCC CAG AAG GAA GCC ATC TCC CCT CCA GAT
Leu Arg Ala Leu Gly Ala Gln Lys Glu Ala Ile Ser Pro Pro Asp

GCG GCC TCA GCT GCT CCA CTC CGA ACA ATC ACT GCT GAC ACT TTC
Ala Ala Ser Ala Ala Pro Leu Arg Thr Ile Thr Ala Asp Thr Phe

CGC AAA CTC TTC CGA GTC TAC TCC AAT TTC CTC CGG GGA AAG CTG
Arg Lys Leu Phe Arg Val Tyr Ser Asn Phe Leu Arg Gly Lys Leu

AAG CTG TAC ACA GGG GAG GCC TGC AGG ACA GGG GAC TCC TCT TCC
Lys Leu Tyr Thr Gly Glu Ala Cys Arg Thr Gly Asp Ser Ser Ser

TCA AAG GCC CCT CCC CCC AGC CTT CCA AGC CCA TCC CGA CTC CCG
Ser Lys Ala Pro Pro Pro Ser Leu Pro Ser Pro Ser Arg Leu Pro

GGG CCC TCG GAC ACC CCG ATC CTC CCA CAA TAA
Gly pro Ser Asp Thr Pro Ile Leu Pro Gln
```

FUSION PROTEIN HAVING THE ENHANCED IN VIVO ACTIVITY OF ERYTHROPOIETIN

TECHNICAL FIELD

The present invention relates to a fusion protein that has an enhanced in vivo activity of erythropoietin that is a novel medicine for the treatment of anemia. More specifically, the present invention relates to a fusion protein that has the highly enhanced in vivo activity of erythropoietin by fusion of EPO molecule with a particular peptide that has half-life elongating activity and is derived from the human body.

BACKGROUND OF THE INVENTION

Erythropoietin (EPO), a glycoprotein having the molecular weight of 30,000 to 34,000, stimulates production of a red blood cell. This protein starts its functions by binding with receptors on erythrocyte precursor cells to result in increase of calcium ion concentration in a cell, increase of biosynthesis of DNA, and stimulation for the formation of hemoglobin and the like. Recombinant human EPO (rhEPO) has been used for the treatment of anemia from renal failure, anemia of a premature baby, anemia from hypothyroidism, anemia from malnutrition, and the like. On the other hand, a clinical use of rhEPO is on the increase. However, the use of rhEPO may cause inconvenience and high costs from the administration of on average 3 times a week due to the short half-life of the rhEPO. Thus, if the in vivo activity of EPO is maintained for a long time, the administration frequency of EPO may be decreased very much.

In vivo activity of EPO is proportional to the in vivo half-life of EPO. It is known that in vivo half-life of EPO is correlated to the content of sialic acid that is located at the terminal of carbohydrate chains of EPO. Therefore, in vivo activity of EPO is highly dependent on the content of carbohydrate chains. On the other hand, the forms of carbohydrate are different according to the kinds of the cells in which EPO is expressed, and therefore, the same glycoproteins may show different carbohydrates if they are expressed in different cells. Some bacteria, for example *E. coli*, are known not to be capable of attaching the carbohydrate chains to the protein. Generally, proteins expressed in *E. coli* do not contain the carbohydrate chains, and thus, *E. coli*-derived EPO, which does not contain the carbohydrate chains, exhibits both enhanced in vitro activity and decreased in vivo activity. Deglycosylated EPO is rapidly eliminated from the human body and has an extremely short half-life. In conclusion, the carbohydrate chains play a very important role in the activity of EPO.

Many studies have been conducted to enhance the activity of EPO. The main method is substitution of some amino acids of EPO by mutagenesis. For example, PCT/US94/09257 filed by Amgen, and titled "Erythropoietin Analog", discloses a method to increase the half-life of EPO by increasing the carbohydrate contents using mutagenesis. Also, an attempt was made to increase the half-life of EPO by formation of EPO dimer. See, A. J. Sytkowski et al., J.B.C. vol. 274, No. 35, pp 24773-24778. Besides, another known method is to enhance in vivo activity of EPO by fusing new amino acids, peptides or protein fragment with EPO and increasing the carbohydrate content, i.e., sialic acid content of EPO. However, all amino acids, peptides or heterogeneous protein fragments may not be used in such methods. In most cases, such fusions result in decrease or loss of inherent activity of protein and may cause a problem of antigenicity when used in vivo.

Fusion proteins or chimeric proteins, etc. have been studied, for example, for follicle stimulating hormone, a sex hormone. See, Furuhashi et al., 1995, *Mol. Endocrinol.*). However, the methods have not been applied to industry since protein modification itself have many risks, and the target protein is not readily obtained without professional skills, and the inherent activity of protein may be decreased or lost to cause the opposite result.

DETAILED DESCRIPTION OF THE INVENTION

The present inventors have extensively studied new methods for enhancing the in vivo activity of EPO by fusing new amino acids, peptides or protein fragment with EPO. As a result, the present inventors have revealed that a fusion protein of EPO with a peptide fragment located at the carboxy terminal (hereinafter, called as "CTP") of β subunit of human chorionic gonadotropin (hereinafter, called as "HCG") has a highly enhanced half-life due to a lot of amino acids that increase glycosylation site without loss of the inherent activity of EPO, and did not cause any antigenicity when applied to the human body. Therefore, the inventors have completed the present invention.

The object of the present invention is to provide a fusion protein having enhanced in vivo activity of human EPO, containing CTP of HCG β subunit fused with human EPO at the carboxy terminal of human EPO.

Another object of the present invention is providing nucleotide sequences encoding the fusion protein, a plasmid containing the nucleotide sequences, and a host cell line transfected with the plasmid.

Moreover, the present invention is providing a process for the preparation of the fusion protein having the enhanced in vivo activity of human EPO by comprising cultivating the above transfected cell line. First, the present invention relates to a fusion protein having an enhanced in vivo activity of human EPO, containing CTP of HCG β subunit fused with human EPO at the carboxy terminal of human EPO. The CTP preferably comprises the amino acid sequence of SEQ ID No. 1 that discloses amino acids of positions 112 to 145, particularly 118 to 145 of HCG β subunit.

Preferably, the fusion protein according to the present invention comprises the amino acid sequence of SEQ ID No. 2.

Second, the present invention relates to nucleotide sequences encoding the fusion protein, a plasmid containing the nucleotide sequences, and a host cell line, preferably CHO (Chinese hamster ovary) cell, transfected with the plasmid.

Third, the present invention relates to a process for the preparation of a fusion protein having an enhanced in vivo activity of human EPO by cultivating the above transfected cell line.

Below, the present invention will be explained in detail.

The present invention comprises the steps of preparation and cloning of human EPO cDNA, construction of an expression vector incorporating EPO-encoding DNA, transfection of animal cells, expression of human EPO, purification of the expressed human EPO, and biological assays thereof.

(1) Preparation and Cloning of Human EPO cDNA

EPO cDNA may be obtained by performing the well-known RT-PCR technique (PreMix Kit™ of Bioneer) using previously prepared EP1 and EC2 primers that are complementary to the both terminals of EPO cDNA in cDNA library of human-derived fetal liver (Invitrogen):

```
EP1: ATGGGGGCACGAATGTCCTGCCTGGCTGG      (SEQ ID NO.3)

EC2: GTCCCCTGTCCTGCAGGCCT               (SEQ ID NO.4)
```

Obtained EPO cDNA is cloned to pGEM-T (Promega), a cloning vector, which is designated as pGEMT-EPO. The pGEMT-EPO is then sequenced, and used as a probe for the following operations.

CTP gene of HCG β unit used in the present invention may be obtained by synthesis and self-priming PCR. Synthesized oligo-nucleotide fragments are EC1, C2, C3 and C4:

```
                                       (SEQ ID NO.5)
EC1: AGGGGAGGCCTGCAGGACAGGGGACTCCTCTTCCT (SEQ ID NO.6)
C2:  GGAAGGCTGGGGGGAGGGGCCTTTGAGGAAGAGGA (SEQ ID NO.7)
C3:  CCAGCCTTCCAAGCCCATCCCGACTCCCGGGGCCC (SEQ ID NO.8)
C4:  TTATTGTGGGAGGATCGGGGTGTCCGAGGGCCCCG
```

1 μl (50 pmole/μl) of each 4 oligomers is taken and PCR is performed using a high fidelity Taq system (BM) for these oligomers.

Figure 1:
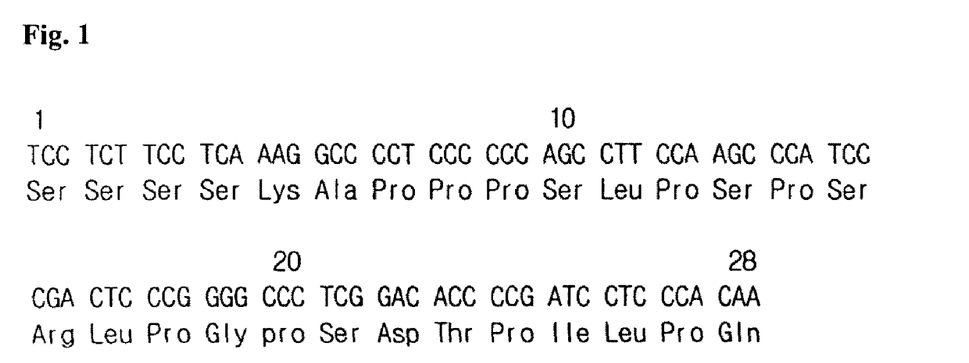
FIG. 1 shows the base (SEQ ID NO: 11) and amino acid (amino acids 7-34 of SEQ ID NO: 1) sequences of carboxy terminal peptide (CTP) of HCG.

About 100 bps of the gene fragment (CTP) are identified in 1% agarose gel. This gene encodes the 28 amino acids (amino acids of positions 118 to 145) of the carboxy terminal of HCG β subunit (Refer to FIG. 1).

A PCR is performed using pGEMT-EPO as a probe and EP1 and EC2 as primers to obtain EPO gene only. The PCR is also performed using both the obtained EPO gene and CTP gene as templates, and EP1 and C4 as primers by a high fidelity Taq system (BM), to obtain 630 bps of the intended fusion gene, ECTP gene. This gene is cloned to a cloning vector, pGEM-T (reverse direction) and then sequenced (designated as pGEMT-ECTP, refer to FIG. 2).

(2) Construction of Expression Vector Incorporating EPO-Encoding DNA pCMV-Script (Stratagene) vector or pcDNA3.1 vector (Invitrogen) are used as an expression vector.

Figure 3:
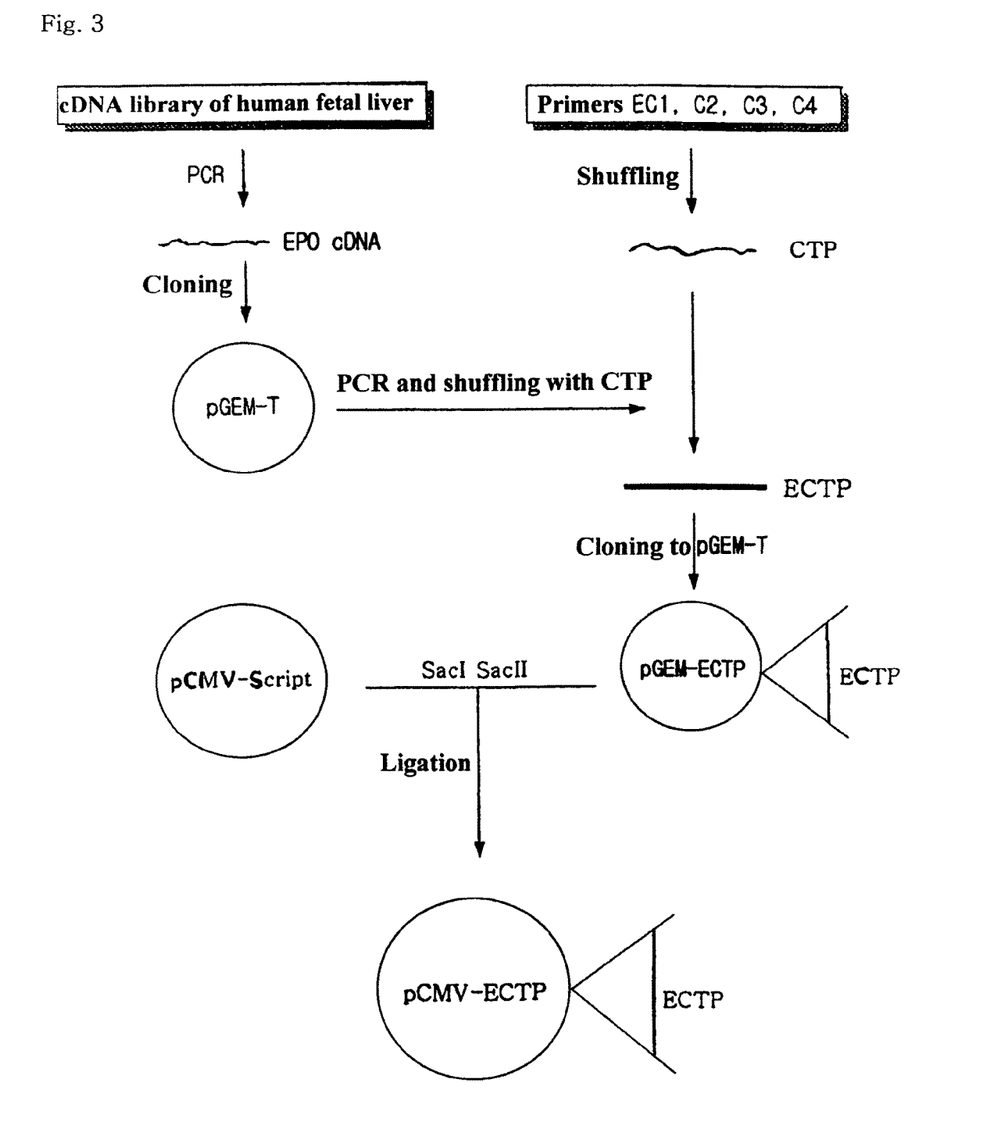
FIG. 3 is a scheme showing the procedures to prepare the expression vector pCMV-ECTP.

(i) When pCMV-Script is Used as an Expression Vector pCMV-Script and pGEMT-ECTP are treated with restriction enzymes Sac I and Sac II, respectively, and the linearized pCMV-Script and ECTP genes are purified using Qiagen gel extraction Kit on agarose gel. After ligation, the ligate was introduced into *E. coli* NM522. Plasmids are isolated from the colonies that are cultivated for one night in LB-kanamycine solid medium, and are treated with restriction enzymes Sac I and Sac II. Colonies having ECTP gene are then screened by 1% agarose gel electrophoresis. This plasmid is designated as pCMV-ECTP (refer to FIG. 3).

(ii) When pcDNA3.1 is Used as an Expression Vector

The PCR is performed using pGEMP-ECTP as a template, and EP11 and EP22 as primers by the high fidelity Taq system (BM), to obtain 630 bps of the intended fusion gene, ECTP gene:

```
EP11: TAAGCTTATGGGGGTGCACGAATGT        (SEQ ID NO.9)

EP22: TGGATCCTTATTGTGGGAGGATCGGGGT     (SEQ ID NO.10)
```

Figure 4:
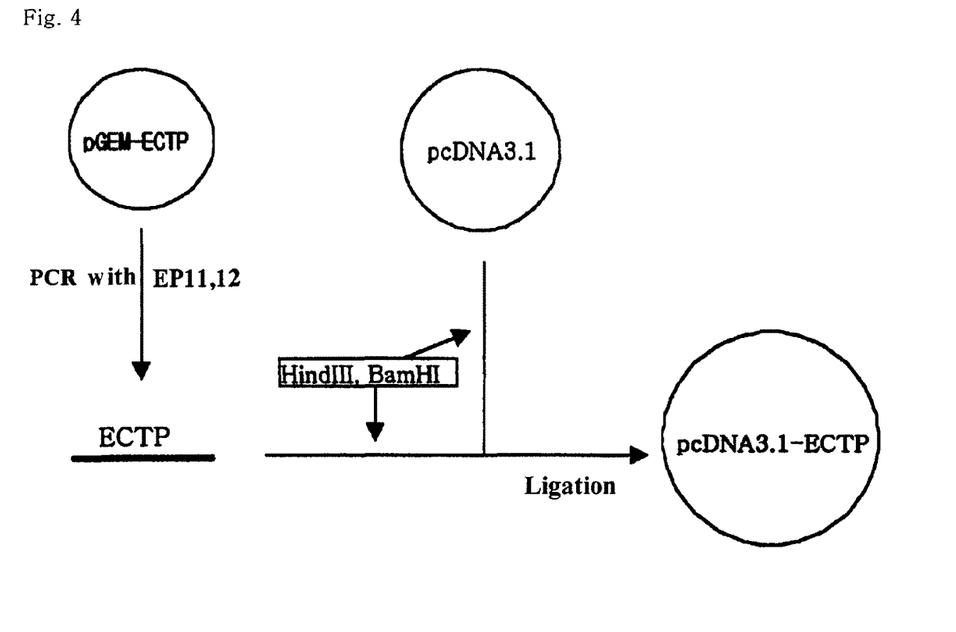
FIG. 4 is a scheme showing the procedures to prepare the expression vector pcDNA3.1-ECTP.

The terminals of ECTP gene have restriction sites of HindIII and BamHI, respectively. pcDNA3.1 and the obtained ECTP gene are treated with restriction enzymes HindIII and BamHI, respectively. The linearized pCMV-Script and ECTP genes are obtained using Qiagen gel extraction Kit on agarose gel, and ligated and introduced into *E. coli* NM522 to obtain transformed *E. coli*. Plasmids are isolated from the colonies that are cultivated for one night in LB-ampicillin solid medium, and are treated with restriction enzymes HindIII and BamHI. Colonies having ECTP gene are then screened by 1% agarose gel electrophoresis. This plasmid is designated as pcDNA3.1-ECTP (Refer to FIG. 4).

(3) Transformation of CHO Cell and the Expression of ECTP (i) When pCMV-Script is Used as an Expression Vector CHO (tk−) cells are prepared by cultivating the CHO cells to reach 40-80% confluency (1~4×10⁵ cells/60 mm dish) at 60 mm cell culture dish. 3 μl of superfection reagent (BM) and 97 μl of cell medium (α-MEM with media, no serum, no antibiotics) are mixed well. The plasmid pCMV-ECTP DNA (>0.1 μg/μl, about 2 μg) is added to this mixture, and reacted for 5~10 minutes at room temperature, and then, added to the above-prepared cells. The medium is refreshed with G418 medium (α-MEM media, 10% serum, and 500 μg/ml of G148) after 1 day. The medium is then refreshed with the G418 medium every day for 7~10 days, and then cells without G418 resistance gene and negative control cells are dead. The selected cells on the G418 medium are sufficiently cultivated and the expressed ECTP protein is identified using EPO ELISA Kit (BM).

(ii) When pcDNA3.1 is Used as an Expression Vector

CHO (DG44) cells are prepared by cultivating the CHO cells to reach 40-80% confluency (1~4×10⁵ cells/60 mm dish) at 60 mm cell culture dish. 3 μl of superfection reagent (BM) and 97 μl of cell medium (α-MEM media, no serum, no antibiotics) are mixed well, and plasmid pcDNA3.1-ECTP DNA (>0.1 μg/μl, about 2 μg) and pLTRdhfr26 (ATCC37295, 0.2 μg) are added to the obtained mixture, reacted for 5~10 minutes at room temperature, and then, added to the above-prepared cells. The medium is refreshed with the G418 medium (α-MEM with media, 10% FBS) after 1 day. The medium is then refreshed with the G418 medium every day for 7~10 days to kill cells without G418 resistance gene and negative control cells. The selected cells on G418 medium are cultivated sufficiently and the expressed ECTP protein is identified using EPO ELISA Kit (BM).

(4) Purification of the Expressed ECTP

Affinity resin for the isolation and purification is prepared using anti-EPO monoclonal antibody (R&D Systems) as follows:

0.3 g of CNBr-activated Sepharose CL 4B is swelled for 20 minutes in 1 mM HCl, and the resin is moved to a column, and washed with 1 mM HCl. The resin is washed with 4 ml of coupling buffer (0.1 M NaHCO₃, 0.5M NaCl, pH 8.3), and immediately mixed with anti-EPO monoclonal antibody (500 μg/vial) contained in 4 ml of coupling buffer in a tube, and reacted at room temperature for 2 hours with stirring the tube. Refreshed with Blocking Buffer (0.2 M glycine, pH 8.0), the resin reacts at room temperature for 2 hours with stirring the tube. Then, the tube is washed with 6.5 ml of coupling buffer, 6.5 ml of acetate buffer (0.1 M acetic acid, 0.5 M NaCl, pH 4) and 6.5 ml of coupling buffer in turn. After the column is prepared, purification of the expressed ECTP is performed as described below.

The cells are cultivated in serum free medium for 1 day, and the medium without cells are concentrated to about 5 folds using Centriprep™ (Millipore, MWCO 10,000). This is then loaded to the column equilibrated with PBS at the flow rate of 20 ml/hr, and washed again with PBS. The column is then washed with the dissolution buffer (0.1M glycine, pH 2.8) and the eluent is immediately titrated with 1M Tris-HCl to pH 7.5. The purity is at least 97% when analyzed by SDS-PAGE and silver staining.

(5) Measurement of Activity by the Bioassay Method and Biochemical Analysis

In vitro biological activities of the expressed and properly purified EPO and ECTP are measured using mouse spleen cells treated with phenylhydrazine. The activity of ECTP is shown to be higher than that of EPO, which demonstrates that the attached CTP in the ECTP may not inhibit the activity of EPO.

IEF (Isoelectric focusing) is performed to ensure the existence of carbohydrate, that is, sialic acid that is located at the terminal of carbohydrate and is known to play an important role in the in vivo activity of EPO. The increase of sialic acid content will move the protein to the low pH due to the strong negative charge of sialic acid. IEF gel patterns (Novex) demonstrate that the ECTP moves to the lower pH than the EPO. This indicates that the in vivo activity of ECTP may be far more prolonged than the activity of EPO.

(6) Pharmacokinetic Experiments

Pharmacokinetic experiments are performed to test whether the prepared candidate substance has prolonged in vivo activity. The candidate substance is intravenously administered to 4 mice at the amount of 20 units/mouse. After sampling blood from the mice, the concentrations of EPO and ECTP are determined using an EIA Kit of Boehringer Manheim. The candidate substance, ECTP, shows a far longer half-life than the control, EPO (Refer to FIG. 6).

BRIEF EXPLANATION OF THE DRAWINGS

FIG. 2 shows the base (SEQ ID NO: 12) and amino acid (SEQ ID NO: 2) sequences of the ECTP that is a fusion protein of EPO and CTP;

BEST MODE FOR CARRYING OUT THE INVENTION

The present invention will be explained in more detail with reference to the following examples. However, the scope of the present invention is not or should not be limited to the examples.

Example 1

Preparation and Cloning of Human EPO cDNA

EPO cDNA was obtained by performing the well-known RT-PCR technique (PreMix Kit™ of Bioneer) in the cDNA library of the human-derived fetal liver (Invitrogen) using previously prepared EP1 and EC2 primers that are complementary to both terminals of EPO cDNA. PCR was performed in 30 cycles under the condition of 55° C. for 35 seconds for annealing, 72° for 40 seconds, and 94° C. for 20 seconds to obtain EPO cDNA. The obtained EPO cDNA was cloned to pGEM-T (Promega), a cloning vector. That is, the PCR products were run on 1% agarose gel, and the separated EPO cDNA was ligated into pGEM-T. The recombined pGEM-T was then introduced into E. coli NM522 to obtain transformed E. coli. Plasmid DNAs were purified from the white colonies that are cultivated for one night in LB-ampicilline solid medium containing X-gal/IPTG, and were treated with restriction enzymes Sac I and Sac II to screen the colonies containing EPO cDNA. The obtained plasmid is designated as pGEMT-EPO.

The CTP gene of HCG β unit was obtained by nucleotide synthesis and self-priming PCR. Synthesized oligonucleotide were EC1, C2, C3 and C4. 1 μl (50 pmole/μl) of each 4 gene was taken by and PCR was performed in 15 cycles under the conditions of 55° C. for 40 seconds for annealing, 72° for 40 seconds, and 94° C. for 20 seconds. About 100 bps of DNA fragment were identified on 1% agarose gel. This gene encodes the 28 amino acids of the carboxy terminal of HCG β subunit (Refer to FIG. 1).

The PCR was performed under the same condition as described above using pGEMT-EPO as a template and EP1 and EC2 as primers to obtain EPO gene only. ECTP gene of 630 bps was obtained by performing the PCR in 30 cycles under the conditions of 58° C. for 40 seconds for annealing, 72° for 60 seconds, and 94° C. for 20 seconds using EPO together with CTP as templates, and EP1 and EC2 as primers. This gene was cloned to the cloning vector pGEM-T in the same manner as mentioned above, and then sequenced (designated as pGEMT-ECTP, refer to FIG. 2).

Example 2

Construction of an Expression Vector pCMV-ECTP pCMV-Script (Stratagene) was used as an expression vector. pCMV-Script and pGEMT-ECTP were treated with restriction enzymes Sac I and Sac II, respectively, and the linearized pCMV-Script and ECTP genes were obtained by the Qiagen gel extraction Kit on agarose gel. After ligation, the ligate was introduced into E. coli NM522. Plasmids were isolated from the colonies that were cultivated for one night in LB-kanamycine solid medium, and were treated with restriction enzymes Sac I and Sac II. The colonies having ECTP gene were then screened by 1% agarose gel electrophoresis. This plasmid is designated as pCMV-ECTP (refer to FIG. 3).

Example 3

Construction of an Expression Vector pcDNA3.1-ECTP pcDNA3.1 (Invitrogen) was used as an expression vector. PCR was performed using the pGEMP-ECTP as a template, EP11 and EP22 as primers, and high fidelity Tag system (BM), to obtain 630 bps of the intended fusion gene. The terminals of the ECTP gene have restriction sites for HindIII and BamHI, respectively. pcDNA3.1 and the obtained ECTP gene were treated with restriction enzymes HindIII and BamHI, respectively. The linearized pCMV-Script and ECTP genes were obtained by the Qiagen gel extraction Kit on agarose gel. After ligation, the ligate was introduced into E. coli NM522. Plasmids were isolated from the colonies that are cultivated for one night in LB-ampicillin solid medium, and were treated with restriction enzymes HindIII and BamHI. The colonies containing ECTP gene were then screened by 1% agarose gel electrophoresis. This plasmid is designated as pcDNA3.1-ECTP (Refer to FIG. 4).

Example 4

Transformation of CHO Cell and the Expression of ECTP (i) When pCMV-Script is Used as an Expression Vector CHO (tk−) cells were prepared by cultivating the CHO cells to reach 40-80% confluency (1~4×10$^5$ cells/60 mm dish) at 60 mm cell culture dish. 3 μl of superfection reagent (BM) and 97 μl of cell medium (α-MEM media, no serum, no antibiotics) were mixed well and plasmid pCMV-ECTP DNA (>0.1 μg/μl, about 2 μg) was added to this mixture and reacted for 5~10 minutes at room temperature, and then, added to the above-prepared cells. After one day, the medium was refreshed with the G418 medium (α-MEM media, 10% serum, and 500 μg/ml of G418). The medium was then refreshed with the G418 medium every day for 7~10 days to kill cells without G418 resistance gene and negative control cells. The selected cells on G418 medium were sufficiently cultivated and the expressed ECTP protein was identified using EPO ELISA Kit (BM).

(ii) When pcDNA3.1 is Used as an Expression Vector

CHO (DG44) cells were prepared by cultivating the CHO cells to reach 40-80% confluency (1~4×10$^5$ cells/60 mm dish) at a 60 mm cell culture dish. 3 μl of superfection reagent (BM) and 97 μl of cell medium (α-MEM with media, no serum, no antibiotics) were mixed well and plasmid pcDNA3.1-ECTP DNA (>0.1 μg/μl, about 2 μg) and pLTRdhfr26 (ATCC37295, 0.2 μg) were added to the obtained mixture and reacted for 5~10 minutes at room temperature, and then, added to the above-prepared cells. The medium was refreshed with G418 medium (α-MEM with media, 10% FBS) after 1 day. The medium was then refreshed with the G418 medium every day for 7~10 days to kill cells without G418 resistance gene and negative control cells. The selected cells on G418 medium were sufficiently cultivated and the expressed ECTP protein were identified using EPO ELISA Kit (BM).

Example 5

Purification of Expressed ECTP

Affinity resin for the isolation and purification was prepared by the following procedures using an anti-EPO monoclonal antibody (R&D Systems).

0.3 g of CNBr-activated Sepharose CL 4B was swelled for 20 minutes in 1 mM HCl, and the resin was moved to the column, and washed with 1 mM HCl. The resin was washed with 4 ml of coupling buffer (0.1 M NaHCO$_3$, 0.5M NaCl, pH 8.3), and immediately mixed with the anti-EPO monoclonal antibody (500 μg/vial) contained in 4 ml of the coupling buffer in a tube, and reacted for 2 hours at room temperature with stirring the tube. Substituting the buffer with Blocking Buffer (0.2 M glycine, pH 8.0), the reaction was continued for 2 hours at room temperature with stirring the tube. Then, the tube was washed with 6.5 ml of the coupling buffer, 6.5 ml of the acetate buffer (0.1 M acetic acid, 0.5 M NaCl, pH 4) and 6.5 ml of the coupling buffer in turn. After the column was prepared, purification of the expressed ECTP was performed as described below.

Figure 5A:
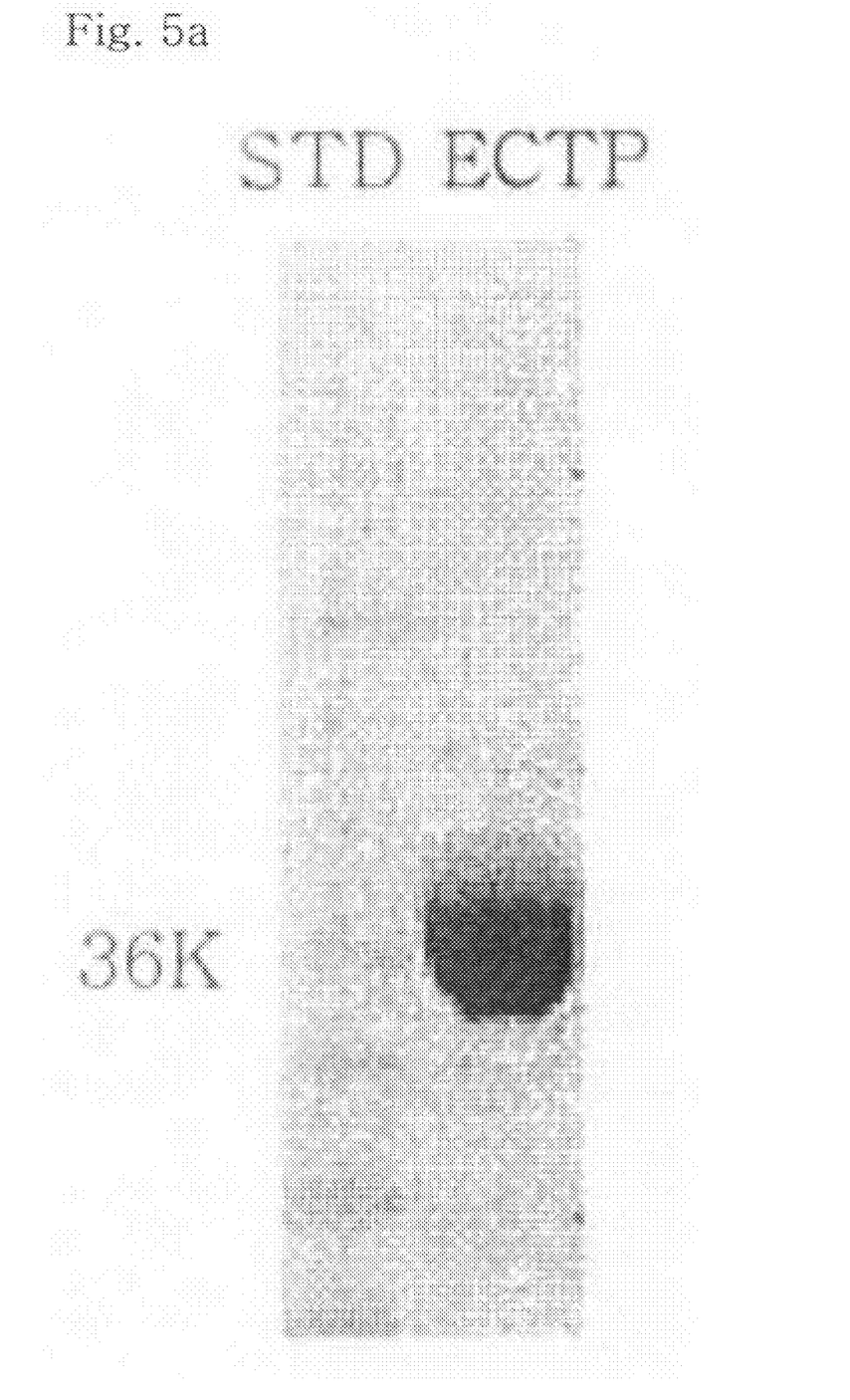
FIG. 5a is an electrophoresis photograph of purified ECTP.

The cells were cultivated on serum free medium for 1 day, and the medium without cells were concentrated to about 5 folds using Centriprep™ (Millipore, MWCO 10,000). This was then loaded to the column equilibrated with PBS at 20 ml/hr of flow rate, and washed again with PBS. The column was then washed with a dissolution buffer (0.1M glycine, pH 2.8) and the eluent is immediately titrated with 1M Tris-HCl to pH 7.5. SDS-PAGE of the purified ECTP was shown in FIG. 5a. The purity was at least 97% when analyzed by SDS-PAGE and silver staining.

Example 6

Measurement of Activity by the Bioassay Method and IEF Analysis

Phenylhydrazine was injected to the mice twice a day for 2 days at the dose of 60 mg/kg. After 3 days, enlarged spleen was separated and ground with a homogenizer to obtain spleen cells. The spleen cells were diluted to 6×10$^6$ cells/ml and 100 μl of the cells were added into 96 well plates. 0~500 mU/ml of standard EPO, and 100 mU/ml of the expressed EPO and ECTP were added to each well and the plate was placed at 37° C. for 22 hours in the CO$_2$ incubator. 50 μl of dimethyl3[H]-thymidine (20 μCi/ml) was added to the plate and further reacted for 2 hours in the same incubator. Each well was then adsorbed onto glass filters (Nunc 1-73164). The filters were washed with physiological saline 3 times and the amount of radioactivity of each filter was measured using β counter. When activities of the moderately purified EPO and ECTP are measured, the activity of ECTP was shown to be comparable to or higher than the activity of EPO, which demonstrated that the CTP attached to EPO might not inhibit the activity of EPO.

Figure 5B:
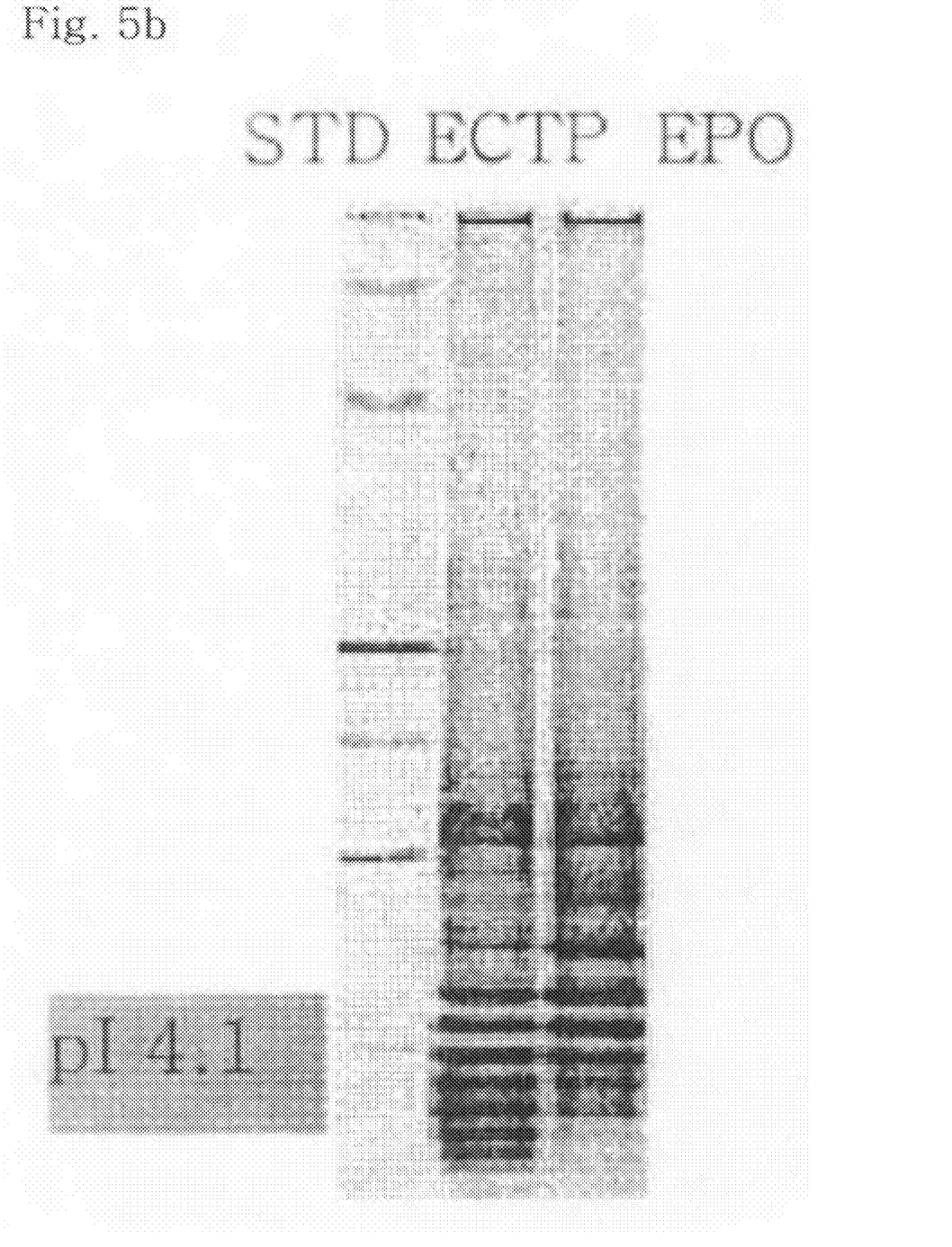
FIG. 5b is an IEF photograph of expressed EPO and ECTP.

The IEF (isoelectric focusing) analysis was performed to ensure the existence of the carbohydrate chains and sialic acids that is located at the terminal of carbohydrate and is known to play an important role in the in vivo activity of EPO. IEF gel patterns (Novex) were shown in FIG. 5b. As shown in FIG. 5b, it was shown that the ECTP moved to the negative pole more than EPO. This indicates that the in vivo activity of ECTP may be far more prolonged than the activity of EPO.

Example 7

Pharmacokinetic Experiments

Figure 6:
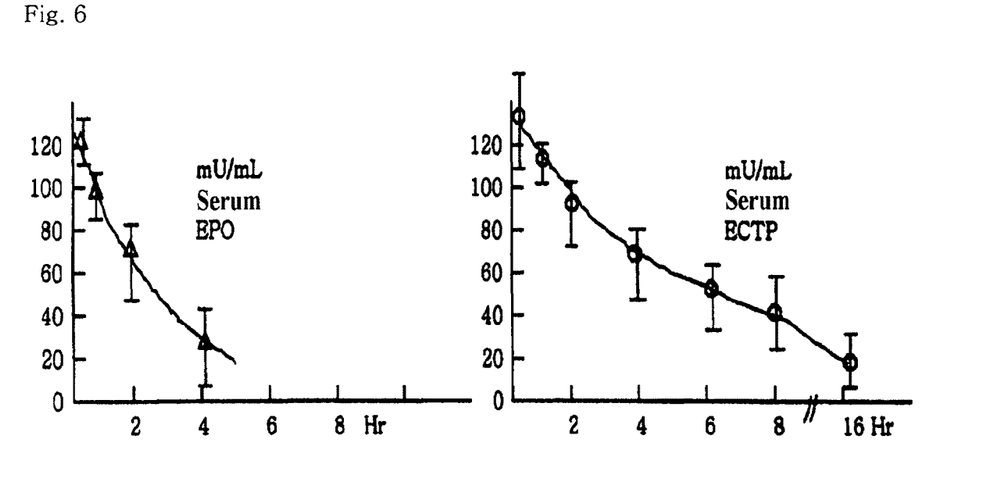
FIG. 6 is a graph showing the pharmacokinetic results of EPO and ECTP.

Pharmacokinetic experiments for the mice were performed to test whether the prepared candidate substance has prolonged in vivo activity. The fusion protein purified by the method of Example 6 was administrated intravenously to 4 mice at the amount of 20 units/mouse. After sampling blood from the mice, concentrations of EPO and ECTP were determined at the interval of 30 minutes for the first 2 hours, and then at the interval of 2 hours using EIA Kit of Boehringer Manheim. The results were shown in FIG. 6. As shown in FIG. 6, the candidate substance, ECTP has a 2.5 times longer half-life than the control, EPO.

INDUSTRIAL APPLICABILITY

The fusion protein according to the present invention has an increased half-life of EPO without influencing the inherent activity of EPO due to presence of the amino acids that increase the carbohydrate chains, and do not cause the problem of antigenicity since CTP is an internal peptide, and thus, is industrially useful.

The invention claimed is:

1. A fusion protein of human erythropoietin (EPO) with a carboxy terminal peptide (CTP) of human chorionic gonadotropin (HCG) β subunit, consistinq of the amino acid sequence of SEQ ID NO: 13.

2. A fusion protein of human erythropoietin (EPO) with a carboxy terminal peptide (CTP) of human chorionic gonadotropin (HCG) β subunit, consisting of the amino acid sequence of SEQ ID NO: 2.

3. A nucleotide sequence encoding the fusion protein according to claim 1 or 2.

4. A process for preparation of the fusion protein of claim 1 or 2 having enhanced in vivo activity of human EPO comprising cultivation of a host cell line transfected with a recombinant vector containing the DNA according to the claim 3.

* * * * *

SEQUENCE LISTING

<160> NUMBER OF SEQ ID NOS: 13

<210> SEQ ID NO 1
<211> LENGTH: 34
<212> TYPE: PRT
<213> ORGANISM: Homo sapiens

<400> SEQUENCE: 1

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

Pro Gln

<210> SEQ ID NO 2
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Ser Ser Ser Ser Lys Ala Pro Pro Pro Ser Leu Pro Ser Pro Ser Arg
        195                 200                 205

Leu Pro Gly Pro Ser Asp Thr Pro Ile Leu Pro Gln
    210                 215                 220

<210> SEQ ID NO 3
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
atgggggcac gaatgtcctg cctggctgg                                       29

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcccctgtc ctgcaggcct                                                 20

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggggaggcc tgcaggacag gggactcctc ttcct                                35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggaaggctgg ggggagggc ctttgaggaa gagga                                 35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccagccttcc aagcccatcc cgactcccgg ggccc                                35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttattgtggg aggatcgggg tgtccgaggg ccccg                                35

<210> SEQ ID NO 9
<211> LENGTH: 25
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 9
taagcttatg ggggtgcacg aatgt                                              25

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggatcctta ttgtgggagg atcggggt                                           28

<210> SEQ ID NO 11
<211> LENGTH: 84
<212> TYPE: DNA
<213> ORGANISM: Homo sapiens
<220> FEATURE:
<221> NAME/KEY: CDS
<222> LOCATION: (1)..(84)

<400> SEQUENCE: 11 tcc tct tcc tca aag gcc cct ccc ccc agc ctt cca agc cca tcc cga         48
Ser Ser Ser Ser Lys Ala Pro Pro Pro Ser Leu Pro Ser Pro Ser Arg
1               5                   10                  15 ctc ccg ggg ccc tcg gac acc ccg atc ctc cca caa                         84
Leu Pro Gly Pro Ser Asp Thr Pro Ile Leu Pro Gln
            20                  25

<210> SEQ ID NO 12
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(660)

<400> SEQUENCE: 12 atg ggg gtg cac gaa tgt cct gcc tgg ctg tgg ctt ctc ctg tcc ctg         48
Met Gly Val His Glu Cys Pro Ala Trp Leu Trp Leu Leu Leu Ser Leu
1               5                   10                  15 ctg tcg ctc cct ctg ggc ctc cca gtc ctg ggc gcc cca cca cgc ctc         96
Leu Ser Leu Pro Leu Gly Leu Pro Val Leu Gly Ala Pro Pro Arg Leu
            20                  25                  30 atc tgt gac agc cga gtc ctg gag agg tac ctc ttg gag gcc aag gag        144
Ile Cys Asp Ser Arg Val Leu Glu Arg Tyr Leu Leu Glu Ala Lys Glu
        35                  40                  45 gcc gag aat atc acg acg ggc tgt gct gaa cac tgc agc ttg aat gag        192
Ala Glu Asn Ile Thr Thr Gly Cys Ala Glu His Cys Ser Leu Asn Glu
    50                  55                  60 aat atc act gtc cca gac acc aaa gtt aat ttc tat gcc tgg aag agg        240
Asn Ile Thr Val Pro Asp Thr Lys Val Asn Phe Tyr Ala Trp Lys Arg
65                  70                  75                  80 atg gag gtc ggg cag cag gcc gta gaa gtc tgg cag ggc ctg gcc ctg        288
Met Glu Val Gly Gln Gln Ala Val Glu Val Trp Gln Gly Leu Ala Leu
                85                  90                  95
```

```
ctg tcg gaa gct gtc ctg cgg ggc cag gcc ctg ttg gtc aac tct tcc       336
Leu Ser Glu Ala Val Leu Arg Gly Gln Ala Leu Leu Val Asn Ser Ser
        100                 105                 110 cag ccg tgg gag ccc ctg cag ctg cat gtg gat aaa gcc gtc agt ggc       384
Gln Pro Trp Glu Pro Leu Gln Leu His Val Asp Lys Ala Val Ser Gly
        115                 120                 125 ctt cgc agc ctc acc act ctg ctt cgg gct ctg gga gcc cag aag gaa       432
Leu Arg Ser Leu Thr Thr Leu Leu Arg Ala Leu Gly Ala Gln Lys Glu
    130                 135                 140 gcc atc tcc cct cca gat gcg gcc tca gct gct cca ctc cga aca atc       480
Ala Ile Ser Pro Pro Asp Ala Ala Ser Ala Ala Pro Leu Arg Thr Ile
145                 150                 155                 160 act gct gac act ttc cgc aaa ctc ttc cga gtc tac tcc aat ttc ctc       528
Thr Ala Asp Thr Phe Arg Lys Leu Phe Arg Val Tyr Ser Asn Phe Leu
                165                 170                 175 cgg gga aag ctg aag ctg tac aca ggg gag gcc tgc agg aca ggg gac       576
Arg Gly Lys Leu Lys Leu Tyr Thr Gly Glu Ala Cys Arg Thr Gly Asp
            180                 185                 190 tcc tct tcc tca aag gcc cct ccc ccc agc ctt cca agc cca tcc cga       624
Ser Ser Ser Ser Lys Ala Pro Pro Pro Ser Leu Pro Ser Pro Ser Arg
        195                 200                 205 ctc ccg ggg ccc tcg gac acc ccg atc ctc cca caa taa                   663
Leu Pro Gly Pro Ser Asp Thr Pro Ile Leu Pro Gln
        210                 215                 220
```

<210> SEQ ID NO 13
<211> LENGTH: 226
<212> TYPE: PRT
<213> ORGANISM: Artificial Sequence
<220> FEATURE:
<223> OTHER INFORMATION: Description of Artificial Sequence: Synthetic
      fusion protein of erythropoietin (EPO) and carboxy terminal
      peptide (CTP) of human chorionic gonadotropin (HCG) beta subunit

<400> SEQUENCE: 13

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

-continued

```
Asp Pro Arg Phe Gln Asp Ser Ser Ser Lys Ala Pro Pro Ser
        195             200             205

Leu Pro Ser Pro Ser Arg Leu Pro Gly Pro Ser Asp Thr Pro Ile Leu
        210             215             220

Pro Gln
225
```